(12) United States Patent
Redel (10) Patent No.: US 8,706,196 B2
(45) Date of Patent: Apr. 22, 2014

(54) METHOD FOR SIMULATING A BLOOD FLOW

(75) Inventor: Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 307 days.

(21) Appl. No.: 13/208,451

(22) Filed: Aug. 12, 2011

(65) Prior Publication Data

US 2012/0041301 A1 Feb. 16, 2012

(30) Foreign Application Priority Data

Aug. 13, 2010 (DE) .......................... 10 2010 039 312

(51) Int. Cl.
- *A61B 5/05* (2006.01)
- *A61B 5/02* (2006.01)
- *A61B 5/00* (2006.01)
- *G06K 9/00* (2006.01)
- *G06K 9/20* (2006.01)

(52) U.S. Cl.
USPC ............... 600/425; 600/500; 378/4; 382/130; 382/131; 382/132; 382/283

(58) Field of Classification Search
None
See application file for complete search history.

(56) References Cited

U.S. PATENT DOCUMENTS

| 7,191,110 | B1 | 3/2007 | Alperin et al. | |
|---|---|---|---|---|
| 7,500,784 | B2 | 3/2009 | Grebner | |
| 2006/0184006 | A1 | 8/2006 | Chen | |
| 2008/0292047 | A1* | 11/2008 | Deinzer et al. ................... | 378/4 |
| 2009/0074277 | A1* | 3/2009 | Deinzer et al. ................ | 382/130 |

FOREIGN PATENT DOCUMENTS

| DE | 102007039034 A1 | 5/2009 |
|---|---|---|
| DE | 102008014792 B3 | 6/2009 |
| WO | WO 2009109887 A1 | 9/2009 |

OTHER PUBLICATIONS

David A. Steinman et al.; "Image-Based Computational Simulation of Flow Dynamics in a Giant Intracranial Aneurysm", AJNR Am J Neuroradiol 24: pp. 559-566, Apr. 2003.
C. Karmonik et al.; "Blood Flow in Cerebral Aneurysms: Comparison of Phase Contrast Magnetic Resonance and Computational Fluid Dynamics—Preliminary Experience"; Fortschr Röntgenstr 2008; 180: pp. 1-7.
L. Augsburger et al.; "Methodologies to assess blood flow in cerebral aneurysms: Current state of research and perspectives"; J Neuroradiol—168 (2009), pp. 1-8.

(Continued)

*Primary Examiner* — Long V. Le
*Assistant Examiner* — Bo J Peng (57) ABSTRACT

A method for simulating a blood flow in a vascular segment of a patient is proposed. A 3D image dataset of an examination region is recorded by a radiographic diagnostic device for generating a 3D vascular model. Contrast agent propagation in the examination region is captured by a dynamic 2D angiography method for generating a real 2D angiography recording. A CFD simulation of the blood flow is performed in the 3D vascular model based on a blood flow parameter for generating a virtual 2D angiography recording. A degree of correspondence between the real and the virtual 2D angiography recordings is determined from identical angulation and adjusted recording geometry of the patient and compared with predefinable tolerance values. The CFD simulation is iteratively optimized while changing the blood flow parameter as a function of the comparison. The degree of correspondence is outputted when the optimum CFD simulation is achieved.

14 Claims, 4 Drawing Sheets

(56) References Cited

OTHER PUBLICATIONS

Qi Sun et al.; "Quantitative evaluation of virtual angiography for interventional X-ray acquisitions"; Proceedings of the Sixth IEEE international conference on Symposium on Biomedical Imaging: From Nano to Macro table of contents; Boston, Massachusetts, USA, pp. 895-898; 2009.

C.M. Strother et al.; "Parametric Color Coding of Digital Subtraction Angiography"; AJNR Am J Neuroradiol 2010 www.ajnr.org pp. 1-6.

* cited by examiner

METHOD FOR SIMULATING A BLOOD FLOW

CROSS REFERENCE TO RELATED APPLICATIONS

This application claims priority of German application No. 10 2010 039 312.6 filed Aug. 13, 2010, which is incorporated by reference herein in its entirety.

FIELD OF THE INVENTION

The invention relates to a method for simulating a blood flow in a vascular segment of a patient during angiography examinations.

BACKGROUND OF THE INVENTION

"Computational Fluid Dynamics", also known as CFD for short, is a method for simulating the blood flow in a vascular section or vascular segment of a blood vessel which contains a pathological, i.e. a morbid change. Such a pathological change in the vascular section exists for example in the form of an aneurysm, i.e. a morbid, locally delimited, frequently bag-like enlargement. An aneurysm can occur in particular in a blood vessel in the region of the brain or of the heart; however, the occurrence of an aneurysm is generally not restricted to a specific region of the body. The clinical significance of an aneurysm, which for example is localized in the brain, arises in particular from the risk of a rupture, i.e. the formation of a tear or burst, which for example can result in hemorrhages and thromboses. In modern medicine, the dynamics of the blood flow in an aneurysm are frequently considered to be a major factor in the pathogenesis of the aneurysm, i.e. in its formation and development.

This simulation of the blood flow by CFD methods imparts a three-dimensional distribution of the flow parameters, such as for example WSS (Wall Shear Stress), along the surface of the vascular lumen.

DE 10 2008 014 792 B3 describes such a method for simulating a blood flow in a vascular section, wherein a captured image of a vascular region including the vascular section is obtained, a 3D vascular section model is determined from the captured image, a number of blood flow parameters are read in, the blood flow is simulated in the vascular section model with the inclusion of the or every blood flow parameter and a number of hemodynamic parameters are output. It is here provided that the captured image is obtained with an implant used in the vascular section such that image data of the implant is included, and that the 3D vascular section model is determined having regard to the image data of the implant used. Furthermore, a corresponding apparatus for simulating a blood flow in a vascular section is specified.

As is known from the article "Image-Based Computational Simulation of Flow Dynamics in a Giant Intracranial Aneurysm" by D. A. Steinmann et al. [1], a number of what are known as hemodynamic parameters are related to a growth and a burst of the aneurysm. A hemodynamic parameter is understood in particular as a parameter which relates to the hemodynamics, i.e. fluid mechanics, of the blood. In the cited article a pressure, a stress and shear stress affecting the vascular wall, as well as a flow rate, are mentioned among other things as hemodynamic parameters. In order to extrapolate such hemodynamic parameters, the blood flow in a vascular section which for example includes the aneurysm, is for example simulated.

In this article by D. A. Steinmann et al. [1] a 3D vascular section model is determined to this end from a 3D captured image which was obtained by means of rotational angiography. The blood flow in the 3D vascular section model is simulated using the CFD method. The simulation is performed here on the assumption of rigid vascular walls and a constant blood viscosity. CFD is a method of numeric flow simulation. The model equations used in numeric fluid mechanics are mostly based on a Navier-Stokes equation, on an Euler equation or on a potential equation.

This method of blood flow simulation is currently being employed in a number of experimental studies. A major restriction is that in this specific application on humans not all basic conditions necessary for the simulation are sufficiently precisely known on an individual patient basis. Hence it is difficult to validate the method and in the past this has not been done.

This means that the resulting flow results for the individual patient may be incorrect. Important basic conditions here include the geometry of the vascular section with aneurysm, the inflow and outflow values of the blood which change over time (speed, volume, etc.), the characteristics of the blood and the local elastic characteristics of the vascular wall.

To perform such rotational angiography to generate 3D captured images in order to obtain a 3D vascular section model, use is made of X-ray systems, the typical important features of which can for example be at least one C-arm, which can be robot-controlled and to which an X-ray tube and a radiographic image detector are attached, a patient support table, a high-voltage generator for generating the tube voltage, a system control unit and an imaging system including at least one monitor.

Figure 1:
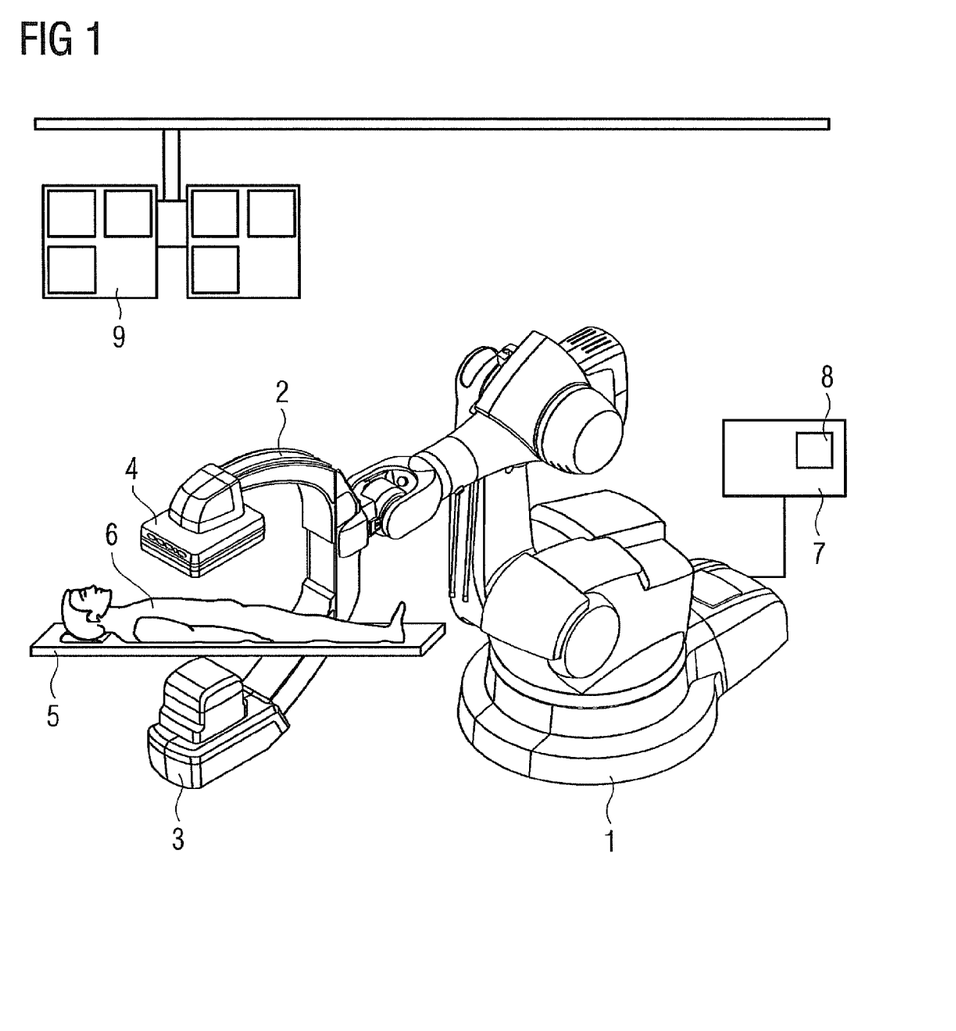
FIG. 1 shows a known X-ray system with an industrial robot as a support apparatus for a C-arm.

Such a typical X-ray system with a robot-mounted C-arm shown as an example in FIG. 1 for example has a C-arm 2 rotatably mounted on a stand in the four of a six-axis industrial or buckling arm robot 1, with an X-ray radiation source, for example a radiographic tube unit 3 with X-ray tube and collimator, and a radiographic image detector 4 as an image capturing unit being attached to the ends of said C-arm 2.

In general CTA and MRA are also suitable for generating the 3D models. The advantage with C-arm systems is that if necessary the 2D recordings are intrinsically registered. Otherwise this has to be done for all modalities.

Using for example the buckling aim robot 1 known from U.S. Pat. No. 7,500,784 B2 which preferably has six rotary axes and thus six degrees of freedom, the C-arm 2 can be spatially readjusted at will, for example by being rotated about a center of rotation between the radiographic tube unit 3 and the radiographic image detector 4. The inventive X-ray system 1 to 4 can in particular be rotated about centers of rotation and rotary axes in the C-arm plane of the radiographic image detector 4, preferably about the center point of the radiographic image detector 4 and about rotary axes intersecting the center point of the radiographic image detector 4.

The known buckling arm robot 1 has a base frame which for example is permanently mounted on a floor. Attached to this is a carrousel which can rotate about a first rotary axis. Fixed to the carrousel is a robot swing arm which can swivel about a second rotary axis, to which is attached a robot arm which can rotate about a third rotary axis. Fixed to the end of the robot arm is a robot hand which can rotate about a fourth rotary axis. The robot hand has a fixing element for the C-arm 2 which can swivel about a fifth rotary axis and can rotate about a sixth axis of rotation running perpendicular thereto.

The implementation of the radiographic diagnostic device is not reliant on the industrial robot. Standard C-arm devices can also be used.

The radiographic image detector 4 can be a rectangular or quadratic, flat semiconductor detector which is preferably made of amorphous silicon (a-Si). However, integrating and possibly metering CMOS detectors can also be used.

In the beam path of the radiographic tube unit 3 a patient 6 to be examined is placed on a patient support table 5 as an examination object for recording a heart for example. Connected to the radiographic diagnostic device is a system control unit 7 with an image system 8 which receives and processes the image signals from the radiographic image detector 4 (operating elements are for example not shown). The X-ray images can then be viewed on displays of a bank of monitors 9.

In the methods currently used for blood flow simulation not all basic conditions necessary for the simulation are sufficiently precisely known on an individual patient basis in this specific application on humans. Hence it is difficult to validate the method. In the references cited below, different approaches are mentioned which enable CFD simulations to be validated.

In "Blood flow in cerebral aneurysm: Comparison of phase contrast magnetic resonance and computational fluid dynamics—preliminary results" by Karmonik et al. [2] the result of a CFD simulation is compared to MR. The MR measurement itself is however imprecise because of the limited resolution and requires a considerable investment in time. Moreover this examination is virtually never performed on patients.

In "Methodologies to assess blood flow in cerebral aneurysm: Current state of research and perspectives" by Augsburger et al. [3] a procedure using in-vitro transparent vascular models and "Particle Image Velocimetry" (PIV) is described which permits CDF data to be compared to measured data.

However, neither method is suitable for validating the CFD measurement for the individual patient.

In "Quantitative evaluation of virtual angiography for interventional X-ray acquisitions" by Sun et al. [4] a method is described which is suitable for verifying CFD simulations for the individual patient in a particular way. To this end the CFD simulation is used to create a virtual angiography which can be compared to a genuine angiography recording of the patient. The result is a qualitative comparison in 2D. A description is additionally given of how to generate a center line and create a flow map along this center line in both angiography recordings. These two lines can be used to perform a quantitative comparison in 1D (along the line), which can be specified in the form of a relative mean quadratic error.

SUMMARY OF THE INVENTION

The object of the invention is to design a method for simulating a blood flow in a vascular segment of a patient during angiography examinations by a radiographic diagnostic device having a radiographic tube unit and a radiographic image detector, a patient support table and a system control unit, wherein a captured image of an examination region including the vascular segment is obtained, a 3D vascular model is determined from the captured image, a number of blood flow parameters are read in, and with the inclusion of these blood flow parameters the blood flow in the 3D vascular model is. The method enables the CFD simulation results to be validated for the individual patient, or any deviations to be quantitatively determined and used iteratively to improve the CFD simulation.

The object is inventively achieved for a method by the features specified in the independent claim. Advantageous embodiments are specified in the dependent claims.

The object is inventively achieved by the following steps:
a) Recording a 3D image dataset of an examination region including the vascular segment (20) for generating a 3D reconstruction image of the examination region,
b) Generating a 3D vascular model from the 3D image dataset,
c) Capturing a contrast agent propagation in the examination region by means of dynamic 2D angiography methods for generating real 2D angiography recordings,
d) Inputting at least one blood flow parameter,
e) Starting a CFD simulation of the blood flow in the 3D vascular model with the inclusion of the at least one blood flow parameter,
f) Generating virtual 2D angiography recordings from the results of the CFD simulation,
g) Determining a degree of correspondence between the real and the virtual 2D angiography recordings from identical angulation and adjusted recording geometry of the individual patient,
h) Comparing the degree of correspondence with predefinable tolerance values,
i) Iteratively optimizing the CFD simulation while changing the at least one blood flow parameter as a function of the comparison according to step h) and
j) Outputting the degree of correspondence ($B_{i,j}$) for the evaluation of the correspondence between the virtual and the real angiography.

As a result information about the local blood flow, in and out of the vascular segment under consideration, can hereby be iteratively adjusted to the real 2D angiography recordings taken.

In fact a new dimension is introduced with the degree of correspondence. Even if other parameters are normally taken from the 2D angiography, these can currently only influence the CFD simulation if they are also used as simulation-relevant parameters.

The definition of the degree of correspondence and its iterative optimization is not reliant on extracting specific flow information from 2D angiography, since these parameters are very often defective. For some time attempts have been made to measure blood speeds in medical angiographies and to date no method is in use. Thanks to the comparison and the degree of correspondence any target parameters (e.g. contrast agent behavior at the highest point of the aneurysm), however abstract they are for the basic conditions for CFD simulation, can be employed for optimization. The aim is to optimize not the flow parameters (basic conditions or manipulated variables) used for the simulation, but the results of the CFD simulation. These must ultimately correspond to the real world. The person skilled in the art will ensure that no irrelevant conditions are obtained.

Advantageously the recording of a 3D image dataset of an examination region including the vascular segment can be obtained according to step a) by means of a radiographic diagnostic device with a radiographic tube unit and a radiographic image detector, a patient support table and a system control unit.

According to the invention a segmentation of the relevant vascular segment can be performed.

It has proved advantageous if the parameters for correcting each segment are selected individually if the vascular segment has several efferent vessels in which the correspondence in both outflowing vascular segments is different.

According to the invention the time intensity curves can be obtained for CFD simulation according to step e) from two scenes for each pixel or for a combination of several pixels, with at least one characteristic variable being extracted from said curves.

According to the invention, time values, intensity values and/or intensity values at defined times can be extracted as characteristic variables.

Advantageously the degree of correspondence according to step g) can be formed as follows:

$$B_{i,j} = T_{i,j} - T^*_{i,j}$$

with the degree of correspondence and the extracted variables for each pixel i,j from both angiographies.

According to the invention the degree of correspondence according to step g) can be a normalized degree of correspondence.

It has proved advantageous if the degree of correspondence according to step g) is determined for the bolus arrival times.

According to the invention the degree of correspondence according to step j) can be represented as an image and/or color-coded as a two-dimensional field.

Advantageously the 3D vascular model can be a 3D vascular section model or a 3D vascular surface model.

According to the invention, at least one of the following basic conditions can be input as blood flow parameters according to step d):
geometry of the vascular section with aneurysm,
inflow and outflow values of the blood, changing over time,
pressure at the inflow and outflow region,
blood characteristics and
local elastic characteristics of the vascular wall.

It has proved to be advantageous if the pressure difference between inflow region and outflow regions, the flow rate and/or the blood volume are selected as a basic condition as inflow and outflow values of the blood, changing over time.

BRIEF DESCRIPTION OF THE DRAWINGS

The invention is explained in greater detail below on the basis of the exemplary embodiments shown in the drawing.

DETAILED DESCRIPTION OF THE INVENTION

In the inventive method, apparatus and workflow a degree of correspondence between a virtual angiography from a CFD simulation and a real angiography scene is determined and this degree of correspondence is used to purposefully and iteratively optimize the CFD simulation.

This degree of correspondence is based on the comparison between a virtual angiography and a real angiography from identical angulation and adjusted recording geometry of the individual patient. The inventive determination of the degree of correspondence in 2-D is an alternative approach to Sun et al. [4].

Output data for this degree of correspondence is dynamic angiography scenes, which show the diffusion or passage of the contrast agent through the corresponding vascular system. The virtual dynamic angiography S* (the values indicated by * always relate in the following to the data derived from the virtual angiography) is obtained by means of CFD simulation. The time intensity curves $TIC_{i,j}$ and $TIC^*_{i,j}$ are now obtained from these two scenes S and S* for each pixel (or combination of several pixels).

In the next step one or also more characteristic variables can be extracted from these time intensity curves, as described in "Parametric color coding of digital subtraction angiography" by Strother et al. [5]. These can be time values and/or intensity values or intensity values at defined times.

Figure 2:
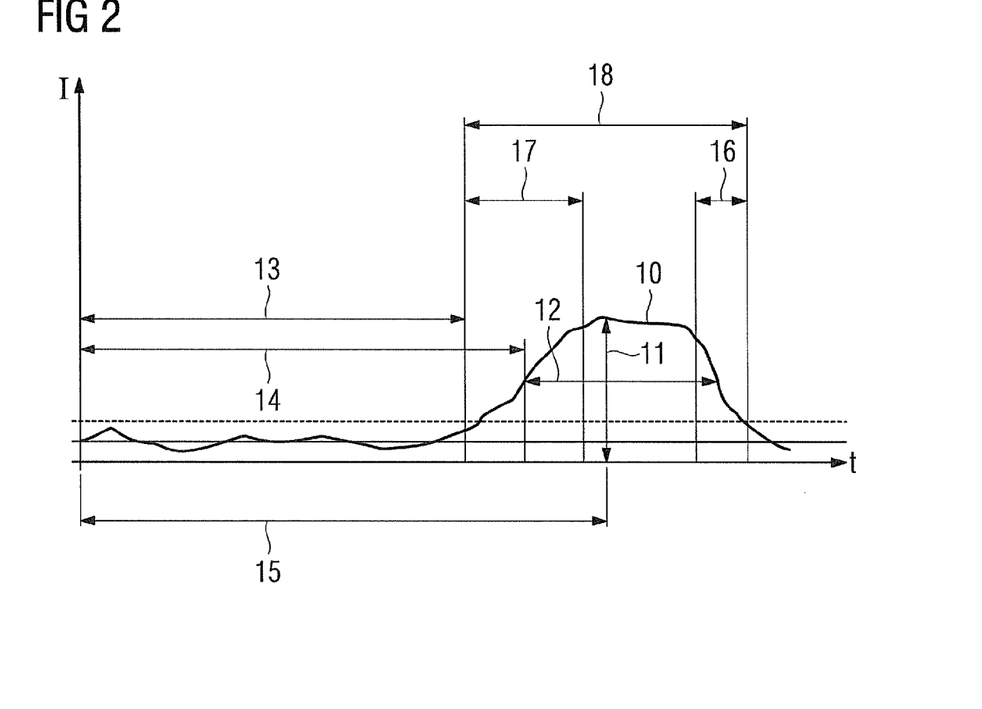
FIG. 2 shows time intensity curves (TIC) with characteristic variables drawn in to explain the invention.

FIG. 2 shows by way of example a time intensity curve (TIC) with drawn-in characteristic variables, in which the blood flow is plotted as intensity I over time t. After a noise-like behavior of the bolus curve 10 the intensity I climbs to the intensity maximum 11 ($I_{max}$), in order then to drop back to a noise level. The bolus curve 10 is furthermore characterized by its half-width 12 (FWHM—Full Width at Half Maximum), which lies between the mean rise and the mean drop of the bolus curve.

The arrival time 13 ($T_{rise}$) is the time that elapses until the occurrence of the contrast agent bolus at the point under examination and thus until the rise in the bolus curve 10. The mean rise time 14 ($T_{rise, FWHM}$) is the time that elapses until the occurrence of the half-width 12 of the bolus curve 10, i.e. until the bolus curve 10 has reached half of the intensity maximum 11 ($I_{max}$). The time until the intensity maximum 11 ($I_{max}$) is called the maximum time 15 ($T_{max}$). The rise time 16 or wash-in time ($T_{wash\ in}$) characterizes the steep rise in the bolus curve 10. The drop in the bolus curve 10 is characterized by the drop time 17 or wash-out time ($t_{wash\ out}$). The duration of the occurrence of the contrast agent bolus is characterized by the bolus or maximum time 18 ($t_{Peak}$).

In the following let $T_{i,j}$ or $T^*_{i,j}$ be the extracted variable for each pixel i,j from both angiographies.

This produces a degree of correspondence $B_{i,j}$ of both angiographies from a mathematical link between both values $T_{i,j}$ or $T^*_{i,j}$, such as a simple subtraction for example.

$$B_{i,j} = T_{i,j} - T^*_{i,j}$$

This degree of correspondence is thus a two-dimensional field, which can be represented for example as an image (e.g. color-coded) and permits an evaluation of the correspondence between the virtual and the real angiography.

Theoretically this degree of correspondence can be determined as in Sun et al. [4] as a mean quadratic error for the entire curves $TIC_{i,j}$ and $TIC^*_{i,j}$. However, this means it is then subsequently not possible to say anything about the nature of the deviation and thus it cannot be used for purposeful control of the CFD optimization.

Until now, however, the two angiography scenes have not been synchronized. In this application there are various excellent vascular regions in the angiography images, among which are the vascular regions into which the blood or the contrast agent flows.

In an improved embodiment regions of interest (ROI) in these vascular regions can be defined in both images. In this case one or more ROI, or corresponding ROI* in the virtual image can be selected such that they cover the vascular inflow regions. In a next step the mean value of the characteristic variable $T_{i,j}$ or $T^*_{i,j}$ under consideration can be determined: $MWT_{i,j}$ or $MWT^*_{i,j}$. From a comparison of these mean values a normalization is calculated in the following. This can be a difference (in the case of temporal values) or a factor e.g. in the case of intensity values, as well as other algorithms.

Thus the normalized degree of correspondence $B_{i,j}$ of both angiography recordings can be balanced:

$$B'_{i,j} = T_{i,j} - T^*_{i,j}(MWT_{i,j} - MWT^*_{i,j})$$

It is especially advantageous if the contrast inflow curve from the real angiography scene is used for the (initial) CFD simulation.

If the simulation of the virtual angiography is performed such that the virtual inflow of the contrast agent matches reality, a normalization can be dispensed with However, it can also happen that both curves are delayed in respect of one another at the time of inflow or have different grayscale values. In this case, depending on the question, normalization will bring an improvement.

Essential for the invention are the definition of a degree of correspondence and the use thereof to assess and optimize the CFD simulation individual to the patient which until now has not been possible in-vivo. In particular the missing information on the local flow, into and out of the vascular segment under consideration, can herewith be adjusted iteratively to the real recorded 2D angiography recordings. This results in an improvement in the CFD results.

This is based on the idea of comparing a virtual angiography obtained from the CFD simulation with the real angiography, determining a degree of correspondence, or if there is a difference optimizing the CFD so that the correspondence becomes better.

In the case of a patient a 3D subtraction angiography with a C-arm system of the cerebral vessels and one (or more) 2D subtraction angiography scenes are recorded.

In a first step a 3D surface model is generated in the computer following a segmentation of the relevant vascular section around an aneurysm, which is then used as geometry for the CFD simulation. Moreover inflow and outflow regions are established.

Figure 3:
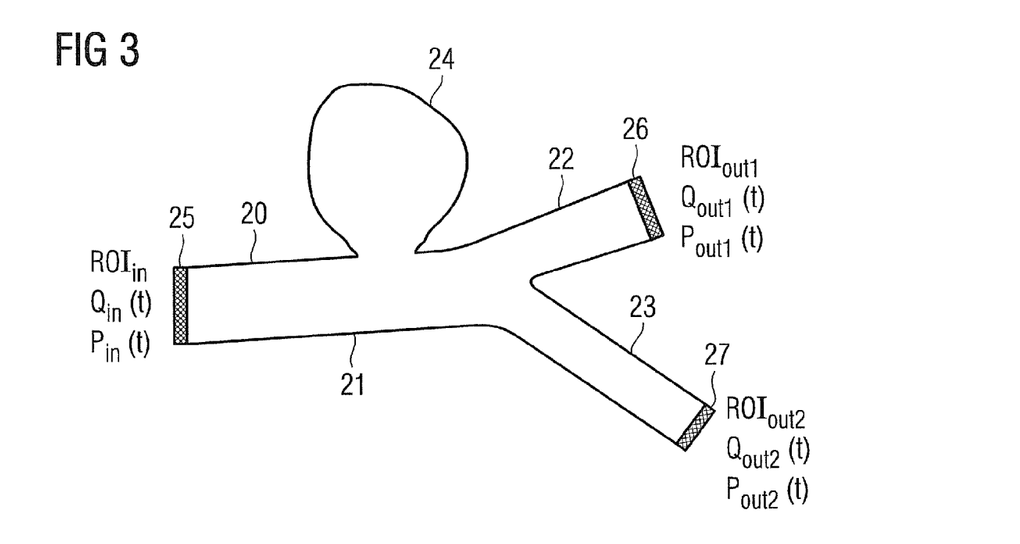
FIG. 3 shows an example of a vascular branching with aneurysm for defining ROIs and the associated basic conditions of flow Q and pressure P.

FIG. 3 shows a vascular segment 20 with an afferent vessel 21 as an example for the definition of the region of interest ROI and the associated basic conditions flow Q and pressure P, which vessel branches into a first efferent vessel 22 and a second efferent vessel 23. The vascular segment 20 furthermore has an aneurysm 24. The inlet to the afferent vessel 21 is formed by an inflow region 25. The outlet of the first efferent vessel 22 is formed by a first outflow region 26 and the outlet of the second efferent vessel 23 by a second outflow region 27. A flow $Q_{in}$ (t) and a pressure $P_{in}$ (t) prevail in the region of interest $ROI_{in}$ of the inflow region 25. In the region of interest $ROI_{out1}$ of the first outflow region 26 a flow $Q_{out1}$ (t) and a pressure $P_{out1}$ (t) are measured and in the region of interest $ROI_{out2}$ of the second outflow region 27 a flow $Q_{out2}$ (t) and a pressure $P_{out\,2}$ (t) are measured.

The selected volume is adjusted here to the 2D angiography, i.e. an angulation and projection geometry corresponding to the 2D angiography are determined in the 3D angiography. If both recordings originate from an examination which involves no movement of the patient this is simple to calculate, but otherwise a registration must be performed. Thus the inflow region 25 and the outflow regions 26 and 27 are now also established in the 2D angiography.

In the following CFD simulation the propagation of an injected contrast agent is simulated, among other things. The temporal dynamics of the contrast agent inflow can be adjusted to the averaged time intensity curve from the 2D angiography. After the simulation a virtual 2D angiography is calculated by means of known angulation and projection geometry using forward projection (DRR), as is described for example in DE 10 2007 039 034 A1.

In a next step the normalized degree of correspondence $B'_{i,j}$ e.g. for the bolus arrival times of both angiographies (real and virtual) is calculated.

If for example the typical vascular segment 20 with the afferent vessel 21, the aneurysm 24 and the two efferent vessels 22 and 23 is considered, a further evaluation for control of an iterative CFD simulation can now take place. To this end the normalized degree of correspondence averaged in the ROI of the outflow regions 26 and 27 of the two efferent vessels 22 and 23 is considered. If it lies within a predefined tolerance, the result of the simulation is satisfactory in respect of these parameters, but otherwise this can be interpreted as a too fast or too slow flow in the entire vascular segment 20. Physically this means that the basic condition of pressure difference between inflow region 25 and outflow regions 26 and 27 was selected suboptimally. This can happen, since the vascular resistance distally to the vascular arborization section under consideration is generally not known.

The tolerances can for example be predefined by a user. It is thereby determined how closely both angiographies, the virtual and the real angiography, must correspond before the user is satisfied.

If the normalized degree of correspondence is positive, the calculated flow is too low and in the subsequent CFD simulation the pressure difference or the pressure conditions must be increased at the outflow regions 26 and 27 (or variables corresponding thereto such as flow rate at the inflow region 25). In the case of a negative value the pressure difference can be reduced correspondingly.

If the correspondence in both outflowing vascular segments $ROI_{out1}$ and $ROI_{out\,2}$ is different, this can be corrected individually for each segment by the individual selection of the parameters.

Another example of this is concerned with the vascular walls. In CFD simulations the vascular walls are increasingly treated elastically. A corresponding analysis can orient the regions of interest along the vascular walls. These are segmented to this end. The degree of correspondence is now determined locally for all pixels along the vascular wall and if values are too large the elasticity for the subsequent CFD simulation is adjusted. It is especially advantageous here if real angiographies from several angulations are present.

Figure 4:
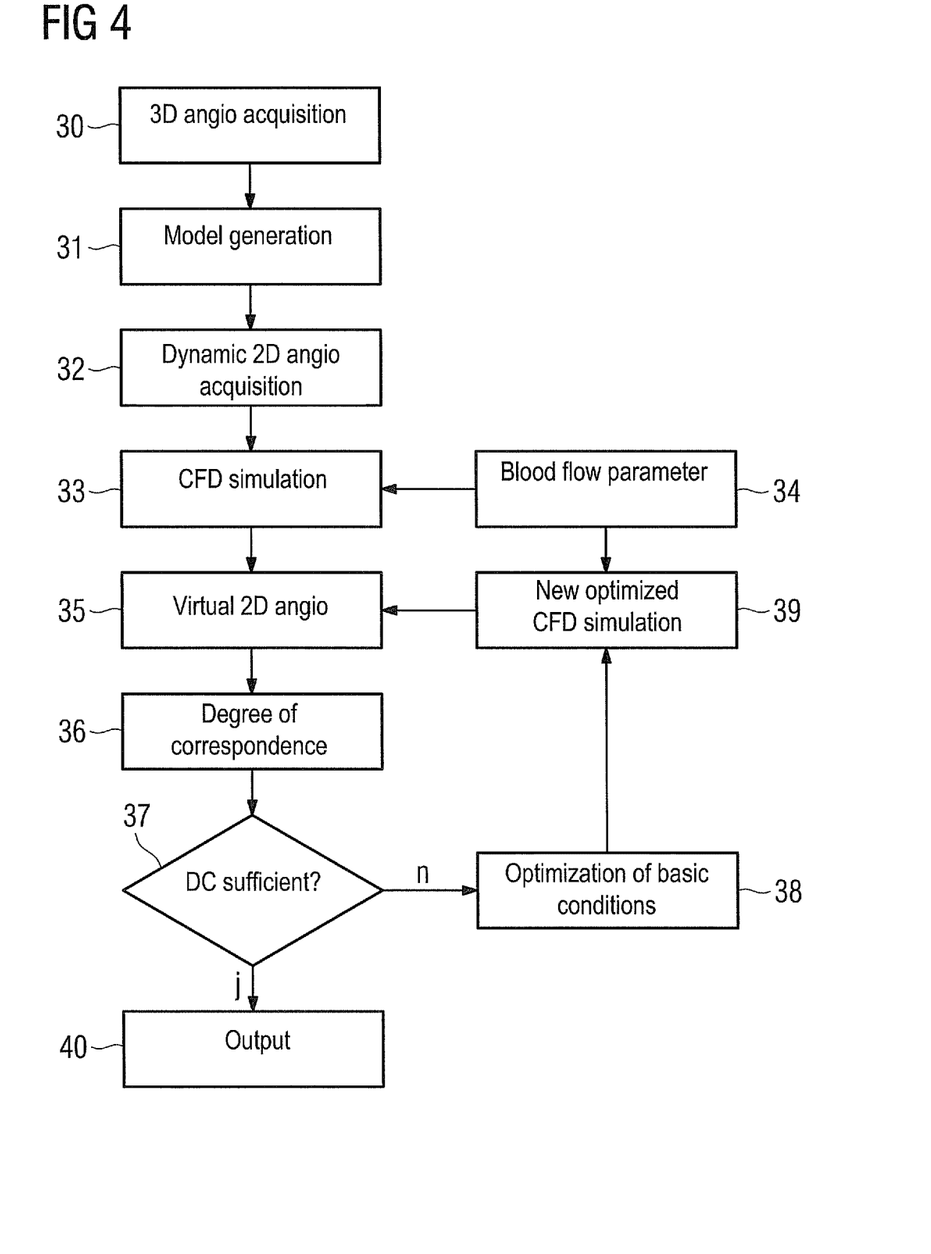
FIG. 4 shows a flowchart of an inventive method sequence and FIG. 5 shows an inventive workflow.

The inventive method is explained in greater detail on the basis of a flow chart shown in FIG. 4. First comes an acquisition 30 of a 3D angiography image dataset for model generation 31. In the further method step a recording 32 of a contrast agent propagation is generated by means of dynamic real 2D angiography. Then a CFD simulation 33 is performed, wherein it is possible to input 34 blood flow parameters as basic conditions. A virtual 2D angiography 35 from angulation identical to the real angiography 32 and adjusted recording geometry of the individual patient is calculated from this data. Then follows a determination 36 of a degree of correspondence based on a comparison between the virtual angiography 35 and the real angiography 32 and then a check 37 to see whether the degree of correspondence is sufficient, i.e. whether the degree of correspondence is within a predefined tolerance. If the degree of correspondence is insufficient, a change 38 in the basic conditions in terms of an optimization is performed. Then follows a new optimized CFD simulation 38, by means of which again a determination 36 is performed, followed by a check 37 on the degree of correspondence. If in contrast the degree of correspondence is sufficient, the degree of correspondence is output 40, for example as a color-coded image and the end of the examination is initiated.

A (percentage) figure, if a global correspondence is considered, as well as a local figure can be described, which then itself can be output as a color map (degree of correspondence). However, it is also possible to describe other values (for example the time difference for the maximum grayscale values).

Figure 5:
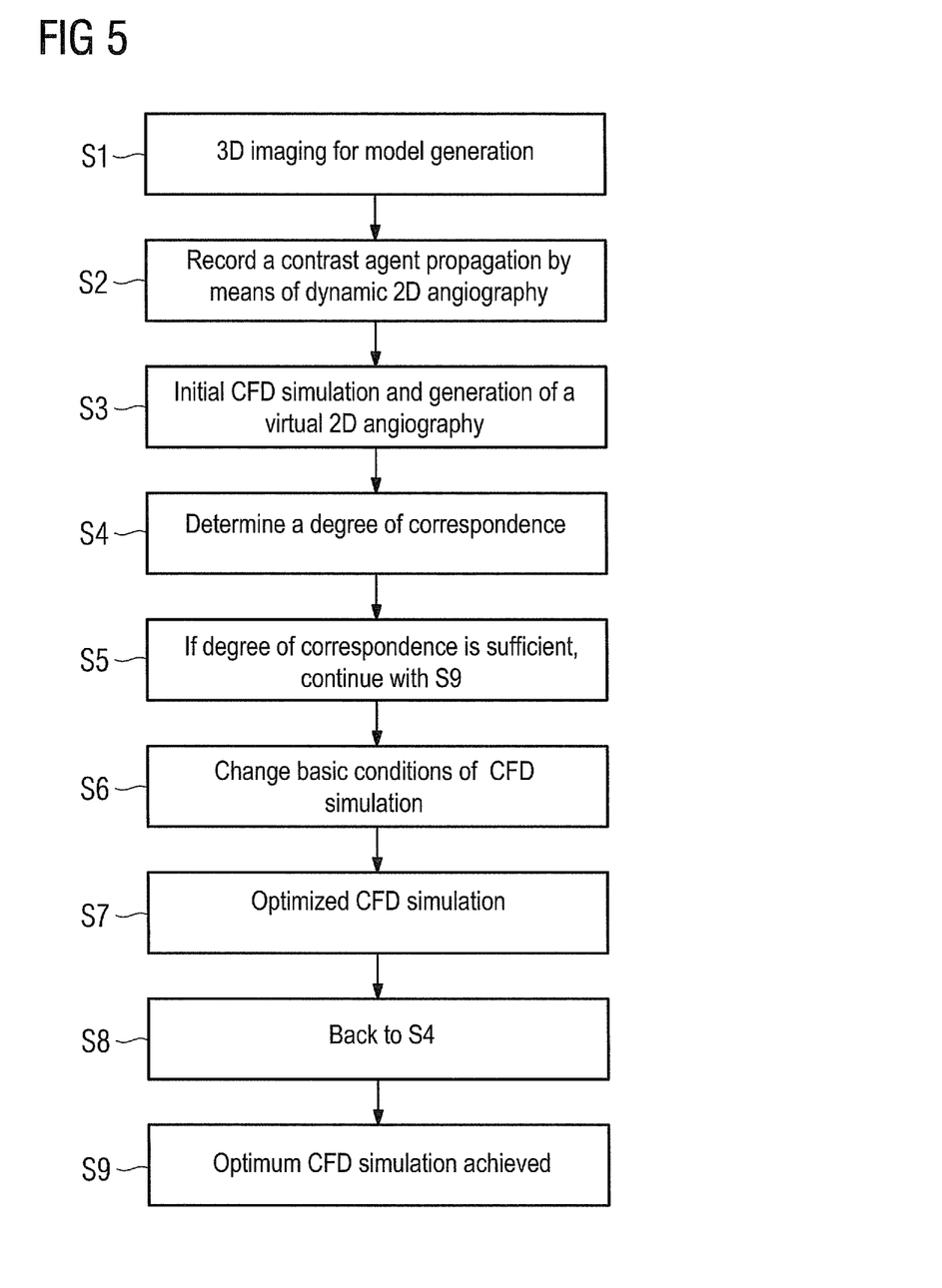

FIG. 5 shows the method sequence or workflow of the inventive method with the following steps in greater detail:

S1) 3D imaging for model generation, e.g. by means of 3D rotational angiography.
S2) Recording a contrast agent propagation by means of dynamic 2D angiography.
S3) Initial CFD simulation and generation of a virtual 2D angiography.
S4) Determining a degree of correspondence between real and virtual 2D angiography.
S5) If degree of correspondence is sufficient, continue with S9).
S6) Changing one or more basic conditions of the CFD simulation according to the result of the degree of correspondence.
S7) Renewed, optimized CFD simulation with basic conditions changed in terms of an optimization.
S8) Back to S4).
S9) Done—optimum CFD simulation was achieved.

The result is an iterative optimization of CFD simulation results based on the comparison between real and virtual 2-DSA recordings on the basis of a determination of a degree of correspondence between both recordings.

REFERENCES

[1] Image-Based Computational Simulation of Flow Dynamics in a Giant Intracranial Aneurysm; David A. Steinman, Jaques S. Milner, Chris J. Norley, Stephen P. Lownie and David W. Holdsworth; American Journal of Neuroradiology (2003), Number 24, pages 559-566
[2] Blood flow in cerebral aneurysm: Comparison of phase contrast magnetic resonance and computational fluid dynamics—preliminary results; C. Karmonik, R. Klucznik, G. Benndorf; Fortschr Röntgenstr 2008; 180:1-7
[3] Methodologies to assess blood flow in cerebral aneurysm: Current state of research and perspectives; L. Augsburger, P. Reymond, E. Fonck, Z. Kulcsar, M. Farhat, M. Ohta, N. Stergiopulos, D. A. Rüfenacht; J. Neurorad.-168: 2009; pages 1-8
[4] Quantitative evaluation of virtual angiography for interventional X-ray acquisitions; Qi Sun, Alexandra Groth, Irina Waechter, Olivier Brina, Jürgen Weese, Til Aach; IEEE; 2009; pages 895-898
[5] Parametric color coding of digital subtraction angiography; C. M. Strother, F. Bender, Y. Deuerling-Zheng, K. Royalty, K. A. Pulfer, J. Baumgart, M. Zellerhoff, B. Aagaard-Kienitz, D. B. Niemann, M. L. Lindstrom; AJNR Am J Neuroradiol; 2010; www.ajnr.org; pages 1-7

The invention claimed is:

1. A method for simulating a blood flow in a vascular segment of a patient during an angiography examination, comprising:
   recording a 3D image dataset of an examination region including the vascular segment for generating a 3D reconstruction image of the examination region;
   generating a 3D vascular model from the 3D image dataset;
   capturing a contrast agent propagation in the examination region by a dynamic 2D angiography method for generating a real 2D angiography recording;
   inputting a blood flow parameter;
   starting a CFD simulation of the blood flow in the 3D vascular model based on the blood flow parameter;
   generating a virtual 2D angiography recording from the CFD simulation;
   determining a degree of correspondence between the real and the virtual 2D angiography recordings based on identical angulation and an adjusted recording geometry of the patient;
   comparing the degree of correspondence with a predefined tolerance value;
   iterating the CFD simulation while changing the blood flow parameter as a function of the comparison until an optimum CFD simulation is achieved; and
   outputting the degree of correspondence between the real and the virtual 2D angiography recordings,
   wherein the 3D image dataset is recorded by a radiographic diagnostic device with a radiographic tube unit and a radiographic image detector, a patient support table and a system control unit.

2. The method as claimed in claim 1, wherein a segmentation is performed in the vascular segment.

3. The method as claimed in claim 1, wherein the vascular segment comprises several efferent vessels and an individual parameter of the blood flow is selected for each efferent vessel.

4. The method as claimed in claim 1, wherein a time intensity curve for extracting a characteristic variable is obtained from the real and the virtual 2D angiography recordings for each pixel or for a combination of several pixels.

5. The method as claimed in claim 4, wherein the characteristic variable comprises a time value or an intensity value at a defined time.

6. The method as claimed in claim 4, wherein the degree of correspondence is obtained as follows:

$$B_{i,j} = T_{i,j} - T^*_{i,j}$$

wherein: $(B_{i,j})$ is the degree of correspondence for each pixel i,j,
   $(T_{i,j})$ is the characteristic variable extracted from the real 2D angiography recording for each pixel i,j, and
   $(T^*_{i,j})$ is the characteristic variable extracted from the virtual 2D angiography recording for each pixel i,j.

7. The method as claimed in claim 1, wherein the degree of correspondence is normalized.

8. The method as claimed in claim 1, wherein the degree of correspondence is determined for a bolus arrival time.

9. The method as claimed in claim 1, wherein the degree of correspondence is outputted as an image.

10. The method as claimed in claim 1, wherein the degree of correspondence is outputted as a color-coded two-dimensional image.

11. The method as claimed in claim 1, wherein the 3D vascular model is a 3D vascular section model.

12. The method as claimed in claim 1, wherein the 3D vascular model is a 3D vascular surface model.

13. The method as claimed in claim 1, wherein the blood flow parameter is selected from the group consisting of: a geometry of the vascular segment with aneurysm, an inflow and an outflow value of the blood flow changing over time, a pressure at an inflow and an outflow region, a blood characteristic, and a local elastic characteristic of a vascular wall.

14. The method as claimed in claim 13, wherein the inflow and the outflow value of the blood flow changing over time comprises a pressure difference between the inflow region and the outflow region, a blood flow rate, and/or a blood volume.

* * * * *